United States Patent [19]

Apairo, Jr. et al.

[11] Patent Number: 4,538,989
[45] Date of Patent: Sep. 3, 1985

[54] DENTAL REAMER

[75] Inventors: Jerry Apairo, Jr.; Derek E. Heath, both of Johnson City, Tenn.

[73] Assignee: Dentsply International, Inc., York, Pa.

[21] Appl. No.: 184,645

[22] Filed: Sep. 16, 1980

Related U.S. Application Data

[63] Continuation-in-part of Ser. No. 80,695, Oct. 1, 1979, abandoned.

[51] Int. Cl.³ .............................................. A61C 5/02
[52] U.S. Cl. ................................................... 433/102
[58] Field of Search ......................................... 433/102

[56] References Cited

U.S. PATENT DOCUMENTS

| 498,554 | 5/1893 | Johanson | 433/102 |
| 1,307,446 | 6/1919 | Kerr | 433/102 |

FOREIGN PATENT DOCUMENTS 2404997  8/1975  Fed. Rep. of Germany ...... 433/102

Primary Examiner—Robert Peshock
Attorney, Agent, or Firm—Luedeka & Neely

[57] ABSTRACT

A dental reamer adapted for removing damaged nerve tissue and dead or injured cell material from the root canal of a tooth is formed with a tapered shank with at least two oppositely disposed continuous helical flutes formed along at least a part of its shank to define two oppositely disposed continuous helical upwardly facing cutting edges.

1 Claim, 5 Drawing Figures

DENTAL REAMER

This application is a continuation-in-part of our co-pending patent application Ser. No. 080,695 filed on Oct. 1, 1979 now abandoned.

The present invention relates to dental reamers for removing decayed or otherwise damaged cell material from the root canal of a tooth.

Removal of a tooth can be often avoided by removing decayed, injured or dead tissue from the root canal of a tooth. Typically, a dentist will first drill into the tooth to locate the root canal and thereafter use a thin file or reamer to remove the decayed, injured or dead tissue. The removal of this tissue is often complicated by the fact that the root canal in not necessarily straight, but follows a somewhat curved path. The reamer or file must therefore be able to follow the curving path of the root canal in order to remove the tissue. Therefore, a dental reamer must be relatively thin and flexible but with a sufficient strength so that it is not easily broken within the root canal of the tooth.

The dentist must be careful not to cut too far or deeply into the tooth. Therefore, the dentist must be able to maintain continuous and constant control over the dental reamer as the cutting proceeds and be able to determine with confidence at any given time how far the dental reamer has penetrated into the tooth.

During the reaming process, the reamed tissue must be removed from the root canal so that the reaming process can continue.

Heretofore known dental reamers are deficient in one or more of these areas of concern. Typically they require a relatively high torsional force to move them in a rotational motion about the longitudinal axis to make them cut into the root canal. This translates into relatively high torsional loads on the shank of the reamer and, therefore, to torsional failure of the reamer. The chances of possible possible in torsion are increased due to the fact, as mentioned above, that root canals are not straight, but curved. Therefore, the shank of the reamer is concurrently subjected to bending loads and torsional loads.

Further, the depth of penetration of some of these dental reamers is difficult to control during the cutting or reaming process because they tend to act in the manner of a self threading screw. Thus, if the dentist momentarily looses his concentration, the reamer could penetrate too far into the tooth causing further damage to the tooth. Also, in order to determine the depth of penetration at any give time, a small, typically rubber, washer is placed on the shank of the reamer at a predetermined location. This is typically done by putting the reamer in a measuring fixture to determine the location for the washer and then placing the washer on the reamer shank and sliding it along the shank to the predetermined location. The washer is held in position on the reamer shank merely by whatever friction there may be between the washer and shank. The washers are not necessarily or usually matched to a particular reamer and, therefore, there is very little friction between the washer and shank. Thus, the washer can easily be inadvertently moved from its predetermined location, particularly during the reaming process. Therefore, the dentist will not be able to determine the depth of penetration with confidence.

The present invention recognizes these deficiencies and problems and provides a solution which is effective and relatively inexpensive and straight forward.

An object of the present invention is to provide a dental reamer which is relatively flexible so that it may follow the path of the root canal, but that has sufficient strength to deminish the chances of breaking within the tooth canal.

Another object of the present invention is to provide a dental reamer which requires a minimal amount of torque for moving it in a rotary motion.

Yet another object of the present invention is to provide a dental reamer which has in increased capacity for removing the tissue from the root canal of the tooth.

A further object of the invention is to provide a dental reamer which gives the dentist better control over the depth of penetration of the reamer into the root canal of the tooth as the cutting proceeds.

A still further object is to provide a dental reamer which allows the dentist to accurately determine with confidence the depth of penetration at any given time.

More particularly, the present invention, in a preferred form, provides a dental reamer having a shank tapered along at least part of its length and terminating at a point. Two oppositely disposed continuous helical flutes are formed in the tapered shank of the reamer and define two oppositely disposed continuous helical cutting edges generally facing upwardly away from the point. The helix angle of each of the flutes decreases over the fluted length of the shank in a direction of convergence of the shank while the pitch of each of the helical flutes is constant over the fluted length of the shank.

A more complete understanding of the present invention will be had by reference to the specification and accompanying drawings wherein like numerals refer to like parts throughout and in which.

Figure 1:
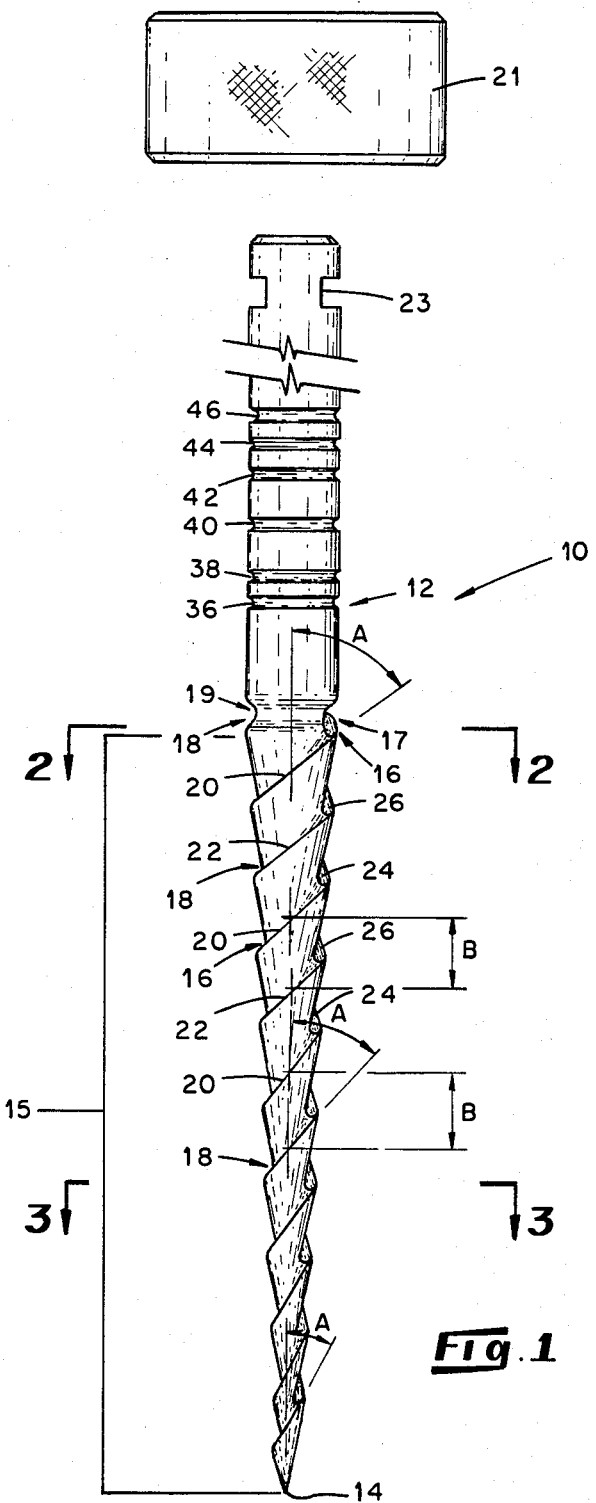
FIG. 1 illustrates a side view of a dental reamer.

With reference to FIGS. 1-5, a dental reamer, generally denoted as a Numeral 10, has a shank 12 tapered along at least a portion of its length 15 and terminating at a point 14. A portion of the shank above the tapered portion is illustrated as being substantially cylindrical. At least two continuous helical flutes 16 and 18 are formed in the tapered portion 15 of the shank 12 and define two helical cutting edges 20 and 22.

Figure 2:
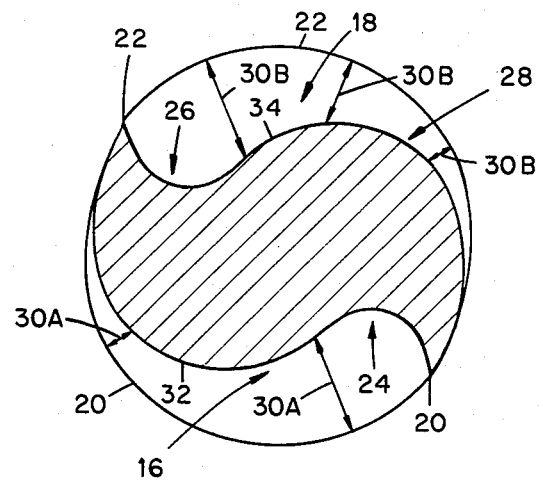
FIG. 2 is an enlarged transverse cross-sectional view taken in direction of arrows 2—2 in FIG. 1.
Figure 3:
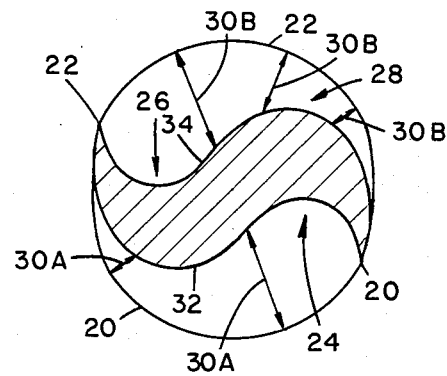
FIG. 3 is an enlarged transverse cross-section taken in the direction of arrows 3—3 in FIG. 1.
Figure 4:
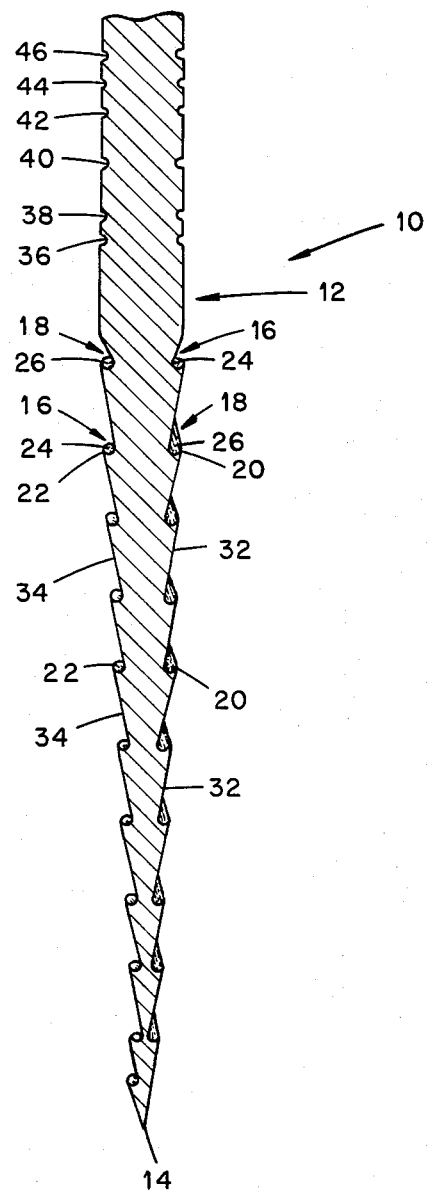
FIG. 4 is a longitudinal cross-sectional view of the dental reamer as illustrated in FIG. 1; and, FIG. 5 is an enlarged view of a portion of the reamer of FIG. 1.

As can be seen in FIGS. 1, 2 and 3, the two continuous helical flutes are a first flute 16 and a second flute 18. The second flute 18 originates, at a region denoted as the numeral 19 in FIG. 1, 180° around the circumference of the shank 12 from the origination, denoted as the numeral 17 in FIG. 1, of the first flute 16. Each of these flutes 16 and 18 is a continuous helical flute from its point of origin, 17 and 19 respectively, to the point 14 of the tapered portion 15 of the shank 12.

As illustrated in FIG. 1, the helical angle, denoted as the letter A, of the first flute 16 and second flute 18 uniformly and continuously decreases over the fluted length 15 of the shaft 12 from its region of origin 17 and 19, respectively, toward the point 14 of the shank 12. In practice it has been determined that a helical angle of about 60° plus or minus 5°, at the top of the fluted length 15 of the tapered shank 12 proximate the regions of origination 17 and 19 of the flutes 16 and 18, and uniformly decreasing to about 25° plus or minus 5°, proximate the point 14 of the tapered shank 12 is preferred.

As can be best seen in FIG. 1, the pitch, denoted by the letter B, of the first flute 16 is the same as the pitch of the second flute 18. Also, the pitch B of each flute 16 and 18 remains constant over the fluted length 15 of the shank 12.

With reference to FIGS. 1 through 5, the first continuous helical flute 16 defines a first sharp continuous helical cutting edge 20, and the second continuous helical flute 18 defines a second sharp continuous cutting edge 22. Each of these cutting edges 20 and 22 is generally directed upwardly or away from the point 14 of the shank 12.

As illustrated, the flutes 16 and 18 are of a right-handed twist and the cutting edges 20 and 22 are of a right-handed cutting direction. However, it is contemplated that the flutes 16 and 18 could follow a left-handed twist and that the cutting edges 20 and 22 then would have a left-handed cutting direction.

With continued reference to FIGS. 1-5, each of the first and second flutes 16 and 18 are undercut. The first flute 16 is undercut in the region, generally denoted as the numeral 24, immediately adjacent the cutting edge 20 to form what is sometimes referred to as a positive rake angle flute. The second flute 18 is also undercut in the region, generally denoted as the numeral 26, immediately adjacent the second cutting edge 22 to form the positive rake angle flute.

Figure 5:
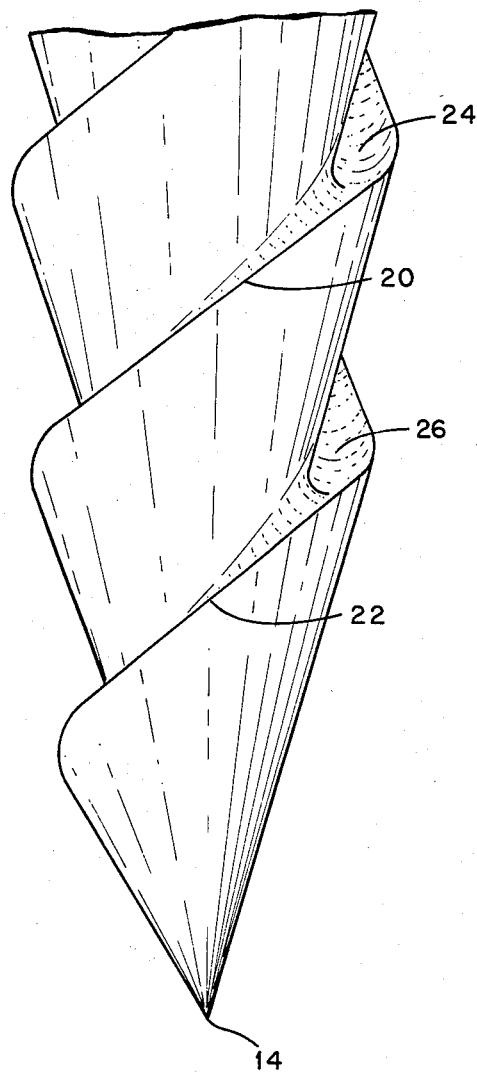

As can be best seen in FIGS. 1 and 5, the first and second flutes 16 and 18 are each of a constant depth along the entire fluted length 15 of the tapered shank 12.

With particular attention to FIGS. 2 and 3, the first and second flutes 16 and 18 cooperate to define a web area 28 therebetween. The web area 28 has a continuous radial web clearance from the first cutting edge 20, generally denoted by the numeral 30A, and a continuous radial web clearance, generally denoted as the numeral 30B, from the second cutting edge 22.

As can be best in FIGS. 1 and 5, the wall 32 of the web 28 formed by the first flute 16 slopes away from the first cutting edge 20 generally inwardly of the shank 12 in a direction toward the point 14 of the shank 12. As illustrated, the wall 32 immediately slopes away from the cutting edge 20. Similarly, the wall 34 of the web 28 formed by the second flute 18 slopes away from the second cutting edge 22 generally inwardly of the shank 12 in a direction toward the point 14 of the shank 12. As illustrated, the wall 34 immediately slopes away from the cutting edge 22.

The first cutting edge 20 is defined between the undercut region 24 and the sloping wall 34 of the web 28 and is, thus, a very sharp edge with minimal or virtually no land area about the outside circumference of the first cutting edge 20. The second cutting edge 22 is also defined between the undercut region 26 and the sloping wall 34 of the web 28 and is, thus, a very sharp edge with a minimal or virtually no land area about the outside circumference of the second cutting edge 22.

With reference to FIG. 1, the dental reamer 10 also includes indicia on at least a portion of the non-fluted part of the shank 12 at predetermined distances from the point 14 of the shank 12. As illustrated, this indicia comprises a plurality of circumferential grooves 36, 38, 40, 42, 44 at spaced apart intervals along the longitudinal axis of the shank 12. The dentist can easily use these circumferential grooves to gauge at a glance the depth of penetration of the reamer 10 into the tooth. In practice it has been deteremined that the spacing between some of the adjacent circumferential grooves should be advantageously different than the spacing between other adjacent circumferential grooves. That is, assuming that there are six such grooves formed in the shank 12, the first groove 36 would be, for example, 18 mm from the point 14 of the shank 12. The next circumferential groove 38 would, for example, be spaced 1 mm from the first circumferential groove 36, and the third circumferential groove 40 would, for example, be spaced 2 mm from the second circumferential groove 36 with the fourth circumferential groove 42 spaced, for example, 2 mm from the third circumferential groove 40, the fifth circumferential groove 44 spaced, for example, 1 mm from the fourth circumferential groove 42, and the sixth circumferential groove 46 spaced, for example, 1 mm from the fifth circumferential groove 44. With such stagered spacing, the dentist can tell at a glance just how far the dental reamer 10 has penetrated the tooth simply by remembering the sequence of spacings and without having to count a plurality of grooves.

Referring to FIG. 1, the cylindrical end of the shank 12 of the reamer 10 opposite the point 14 is illustrated as being formed with two notches 21. The reamer is thus adapted for use in, for example, a power driven dental drill apparatus. Alternatively, a handle 23 is adapted to be attached to the cylindrical end of the shank 12 so that the dental reamer can be used manually.

The sloping web walls 32 and 34 of the first and second flutes 16 and 18 cooperate with the undercut regions 24 and 26 of the flutes 16 and 18 to provide very sharp cutting edges 20 and 22 for cutting into the tissue in the root canal. This coupled with the feature that there is a minimal outside circumferential land, and preferrably virtually no outside circumferential land, at the cutting edges 20 and 22 which would create a frictional interface with the wall of the root canal produce the result that less torque need be applied to the reamer 10 to rotate it about its longitudinal axis to create a cutting or reaming action and, therefore, the shank 12 of the reamer 10 is subjected to less of a torsional load and is less prone to torsional failure or breakage.

The presence of a minimal outside circumferential land at the first and second cutting edges 20 and 22 also serves to enhance the cutting action of the cutting edges by allowing the cutting edge to bite into the tissue in the root canal. A circumferential land, other than a minimal land, adjacent the cutting edges 20 and 22 would result in more of a rubbing action by preventing the cutting edges from bitting into the tissue. Also, a circumferential land in the vicinity of the cutting edges could thereby radially displace the tissue away from and out of contact with the cutting edges. Preferably, as illustrated there is virtually no outside circumferential flange.

The undercut regions 24 and 26 also promote smooth chip formation of the tissue being reamed from the root canal which also contributes to the need for less torque in order to ream the tissue from the root canal.

The decreasing helix angle of the first and second flutes 16 and 18 diminish the tendency of heretofore known reamers to act in the manner of a self-threading screw and, thus, gives the dentist more control over the depth of penetration of the reaming during the reaming procedure.

The undercut regions 24 and 26 of the first and second flutes 16 and 18, respectively, further provide the reamer with an increased capacity for carrying severed tissue out of the root canal continuously while the reaming procedure is taking place and when the reamer is removed from the root canal.

The indicia on the cylindrical portion of the shank 12, illustrated as circumferential grooves 36, 38, 40, 42 and 44, provide the dentist with fixed means for determining with confidence and at a glance, the depth of penetration at any given time.

A dental reamer 10 fabricated of, for example, 302 Stainless steel is preferred to provide strength and flexibility.

By way of example, one size of dental reamer 10 has a fluted length 15 of about 16 mm measured from the point 14. At a location about 1 mm from the point 14 the shank 12 is about 0.1 mm in diameter and at a location about 14 mm from the point 14 the shank 12 is about 0.38 mm in diameter. In a larger size dental reamer 10, for example, the fluted length 15 is about 16 mm measured from the point 14, with a shank diameter of about 0.55 mm at a location about 1 mm from the point 14 and a shank diameter of about 0.83 mm at a location about 14 mm from the point 14. In a third example of a yet different size dental reamer 10, the fluted length 15 is about 16 mm measured from the point 14, with a shank diameter of about 1.4 mm at a location about 1 mm from the point 14 and a shank diameter of about 1.68 mm at a location about 14 mm from the point 14.

The foregoing detailed description is given primarily for clearness of understanding, and no unnecessary limitations should be understood therefrom for modifications will be obvious to those skilled in the art upon reading this disclosure and can be made without departing from the spirit of the invention or the scope of the appended claims.

What is claimed:

1. A dental reamer comprising a shank tapered along at least part of its length and terminating at a point;
    two oppositely disposed continuous helical flutes formed in said tapered shank defining two oppositely disposed continuous helical cutting edges, generally directed away from said point;
    the helix angle of each of said flutes uniformly decreasing over the fluted length of said shank and the pitch of each of said helical flutes being constant over the fluted length of said shank;
    each flute immediately adjacent said cutting edge being undercut to form a positive rake angle cutting edge; and the web defined between said at least two flutes immediately sloping away from said first and said second cutting edges so that there is virtually no outside circumferential land at said cutting edges.

* * * * *